United States Patent
Lebrun et al.

(10) Patent No.: US 11,453,833 B2
(45) Date of Patent: Sep. 27, 2022

(54) LUBRICATING BASE OIL SYNTHESIZED FROM BIOSOURCED POLYOL AND FATTY ACIDS ESTERS

(71) Applicant: Arkema France, Colombes (FR)

(72) Inventors: Stéphanie Lebrun, Serquigny (FR);
Salomé Gravelat, Serquigny (FR);
Guillaume Le, Serquigny (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 17/425,356

(22) PCT Filed: Jan. 29, 2020

(86) PCT No.: PCT/FR2020/050138
§ 371 (c)(1),
(2) Date: Jul. 23, 2021

(87) PCT Pub. No.: WO2020/157433
PCT Pub. Date: Aug. 6, 2020

(65) Prior Publication Data
US 2022/0089964 A1 Mar. 24, 2022

(30) Foreign Application Priority Data

Jan. 29, 2019 (FR) .................................... 1900786

(51) Int. Cl.
| | | |
|---|---|---|
| *C10M 105/38* | (2006.01) | |
| *C10M 105/34* | (2006.01) | |
| *C10N 30/00* | (2006.01) | |
| *C10N 20/00* | (2006.01) | |
| *C10N 20/02* | (2006.01) | |
| *C10N 30/02* | (2006.01) | |
| *C10N 40/08* | (2006.01) | |
| *C10N 40/25* | (2006.01) | |

(52) U.S. Cl.
CPC ........ *C10M 105/38* (2013.01); *C10M 105/34* (2013.01); *C10M 2207/2815* (2013.01); *C10M 2207/2835* (2013.01); *C10N 2020/02* (2013.01); *C10N 2020/081* (2020.05); *C10N 2030/02* (2013.01); *C10N 2030/64* (2020.05); *C10N 2040/08* (2013.01); *C10N 2040/25* (2013.01)

(58) Field of Classification Search
CPC .............. C10M 105/38; C10M 105/34; C10M 2207/2815; C10M 2207/2835; C10N 2020/02; C10N 2020/081; C10N 2030/02; C10N 2030/64; C10N 2040/08; C10N 2040/25
USPC .......................................................... 508/458
See application file for complete search history.

(56) References Cited

U.S. PATENT DOCUMENTS

2010/0166801 A1   7/2010 Puzo et al.
2015/0028252 A1*  1/2015 Saito .................. C10M 171/008
                                                              252/68
2019/0284500 A1*  9/2019 Rached .............. C10M 171/008

FOREIGN PATENT DOCUMENTS

| CN | 101622266 A   | 1/2010  |
| CN | 104262302 A   | 1/2015  |
| EP | 0879872 A1    | 11/1998 |
| EP | 1533360 A1    | 5/2005  |
| EP | 1950218 A1    | 7/2008  |
| WO | 2008090425 A1 | 7/2008  |

OTHER PUBLICATIONS

International Search Report (PCT/ISA/210) and Written Opinion (PCT/ISA/237) dated Apr. 3, 2020, by the European Patent Office as the International Searching Authority for International Application No. PCT/FR2020/050138. (17 pages).
Thomas, Alfred, et al., "Fats and Fatty Oils", Ullmann's Encyclopedia of Industrial Chemistry, Sep. 30, 2015, pp. 1-84, ISBN: 978-3-527-30673-2, XP055634648A, Wiley-VCI Verlag GmbH & Co. KGaA, Weinheim. (84 pages).
Office Action (The First Office Action) dated Apr. 6, 2022 by the China National Intellectual Property Administration in corresponding Chinese Patent Application No. 202080011553.0, and an English Translation of the Office Action. (19 pages).

* cited by examiner

*Primary Examiner* — Prem G Singh
*Assistant Examiner* — Francis C Campanell
(74) *Attorney, Agent, or Firm* — Buchanan Ingersoll & Rooney P.C.

(57) ABSTRACT

The present invention relates to esters of at least one polyol and of a mixture of fatty acids comprising at least one $C_5$-$C_{12}$ saturated fatty acid and at least one $C_{10}$-$C_{12}$ unsaturated fatty acid.

18 Claims, No Drawings

LUBRICATING BASE OIL SYNTHESIZED FROM BIOSOURCED POLYOL AND FATTY ACIDS ESTERS

FIELD OF THE INVENTION

The present invention relates to esters of polyols and a mixture of fatty acids, the use thereof as a lubricant base and the process for the manufacture thereof.

TECHNICAL BACKGROUND

Currently, the lubricant base market is dominated by mineral oils of petroleum origin. In 2008, the European production of lubricants amounted to 4.5 million tonnes per year. These lubricant bases are used in various industries as engine oil, cutting oil for chainsaw chains, oil for offshore oil drilling, hydraulic oil for civil engineering equipment and agricultural machinery, etc.

These mineral oils, once used, are not always recycled and cause environmental pollution due to discharge onto the ground, into sewers, into lakes and rivers. In view of the potential impact of these lubricating oils on the environment, the development of ecological and biodegradable lubricant bases is essential, in particular for applications in which the lubricant is liable to escape into the environment.

The use of plant and animal oils has been known for several years. These oils have the advantage of being ecological. However, they have low thermal stability, low oxidation resistance compared to mineral oils and are liable to hydrolyze in the presence of water.

Biodegradable lubricant compositions comprising products derived from palm oil and polyols such as neopentyl glycol or trimethylolpropane are described in patent application EP 1 533 360. However, such compositions are only suitable for temperatures ranging from 15° C. to 40° C.

In this context, it therefore remains necessary to develop polyol esters, the structure of which may derive from ingredients preferably of renewable origins, having excellent lubricating properties and also being harmless to humans and the environment.

SUMMARY OF THE INVENTION

In the context of the invention, it has been observed that esters of at least one polyol and of a mixture of fatty acids comprising at least one $C_5$-$C_{12}$ saturated fatty acid and at least one $C_{10}$-$C_{12}$ unsaturated fatty acid have excellent properties for applications in lubricants.

The present invention results from the unexpected demonstration, by the inventors, that esters of at least one polyol and of a mixture of fatty acids in which the acids are a mixture of 10-undecylenic acid and n-heptanoic acid that are derived from renewable resources have excellent properties for applications in lubricants.

Thus, the present invention relates to esters of at least one polyol and of a mixture of fatty acids comprising at least one $C_5$-$C_{12}$ saturated fatty acid and at least one $C_{10}$-$C_{12}$ unsaturated fatty acid.

The present invention also relates to the use of esters of at least one polyol and of a mixture of linear fatty acids comprising at least one $C_5$-$C_{12}$ saturated fatty acid and at least one $C_{10}$-$C_{12}$ unsaturated fatty acid as defined above as a lubricant base. The present invention also relates to a lubricant base composition comprising esters of at least one polyol and of a mixture of linear fatty acids comprising at least one $C_5$-$C_{12}$ saturated fatty acid and at least one $C_{10}$-$C_{12}$ unsaturated fatty acid as defined above.

The present invention also relates to a process for preparing esters comprising the esterification of a mixture of linear fatty acids comprising at least one $C_5$-$C_{12}$ saturated fatty acid and at least one $C_{10}$-$C_{12}$ unsaturated fatty acid with at least one polyol, optionally in the presence of a catalyst.

The present invention also relates to esters of at least one polyol and of a mixture of linear fatty acids comprising at least one $C_5$-$C_{12}$ saturated fatty acid and at least one $C_{10}$-$C_{12}$ unsaturated fatty acid which are obtained by the process defined above.

DETAILED DESCRIPTION OF THE INVENTION

The lubricant base compositions according to the invention synthesized from esters of at least one polyol and of a mixture of fatty acids of renewable origin, such as for example erythritol and the mixture of fatty acids in which the acids are a mixture of n-heptanoic acid and 10-undecylenic acid (e.g. a mixture of Oleris® C7 and C11:1 from Arkema), make it possible to achieve properties in terms of thermal stability, oxidation stability, and also viscosity index, which are higher than the usual esters in which the alcohol is not biobased, such as, for example, trimethylolpropane, as is described in detail in the examples below.

Thus, the present invention provides a particular lubricant base composition which offers good thermal stability, better oxidation stability and very good lubricating properties. The term "biodegradable" is used here to denote a compound formed of molecules which can be converted into smaller, less polluting molecules, for example by living microorganisms in the natural environment, such as bacteria, fungi and algae. The end result of this degradation is generally composed of water, carbon dioxide or methane.

Materials, compounds or ingredients that are "derived from renewable resources" or "biobased" are understood to mean renewable natural materials, compounds or ingredients, the stock of which can be reconstituted over a short period on the human timescale. These are in particular raw materials of animal origin or of plant origin. The term "raw materials of renewable origin" or "biobased raw materials" means materials which comprise biobased carbon or carbon of renewable origin. Specifically, unlike materials derived from fossil materials, materials composed of renewable raw materials contain carbon 14 ($^{14}C$). The "content of carbon of renewable origin" or "content of biobased carbon" is determined by application of the standards ASTM D 6866 (ASTM D 6866-06) and ASTM D 7026 (ASTM D 7026-04).

The viscosity of a fluid means the resistance that it puts up against the internal sliding of its molecules while it is flowing. The viscosity is given for a reference temperature. The kinematic viscosity, expressed in m/s², is calculated using the following formula:

$$\nu = \eta/\rho, \text{ where}$$

$\eta$ is the dynamic viscosity in Pa·s; and
$\rho$ is the density of the fluid in kg/m³.

The kinematic viscosity is also expressed in stokes (St) or in centistokes (cSt).

The kinematic viscosity is measured according to the standard ISO 3104.

Oxidation stability can be determined via two measurements: oxygen induction time and oxygen induction temperature. The oxygen induction time and the oxygen induction temperature can be measured in a differential scanning calorimeter (DSC) according to the standard ISO 11357-6: 2018.

The pour point of a product is the minimum temperature at which the product still flows. The pour point is measured according to the standard ISO 3016.

The viscosity index (VI) (unitless) indicates the rate of change in the viscosity of an oil over a given temperature range, usually between 40° C. and 100° C. The viscosity index can be defined as the kinematic viscosity gradient of a material, between 40° C. and 100° C. When the viscosity index is low (less than 100), the fluid displays a relatively large variation in viscosity with temperature. When the viscosity index is high (greater than 150), the fluid has relatively little change in viscosity with temperature. In a variety of applications, a high or very high viscosity index is preferable. The viscosity index is measured according to the test method described in the standard ASTM D 2270.

Esters

The esters according to the invention are formed from at least one polyol and from a mixture of fatty acids comprising at least one $C_5$-$C_{12}$ saturated fatty acid and at least one $C_{10}$-$C_{12}$ unsaturated fatty acid.

According to one embodiment, the esters according to the present invention may be monoesters, diesters, triesters and tetraesters.

The mixture of fatty acids according to the invention is preferably derived from renewable resources. The mixture of fatty acids according to the invention is preferably linear or branched, of plant or animal origin.

The mixture of fatty acids according to the invention preferably consists predominantly of linear fatty acids. Preferably, the mixture of fatty acids according to the invention consists of at least 50% by weight, more preferably from 50% to 70% by weight, even more preferably at least 70% by weight of linear fatty acids relative to the weight of the mixture of fatty acids. More preferably, the mixture of fatty acids consists of 100% of linear fatty acids.

Preferably, linear fatty acids make it possible to increase the viscosity index of the lubricant bases synthesized, to improve the thermal stability thereof and are more readily biodegradable than branched acids, mainly derived from the petroleum industry.

The mixture of fatty acids according to the invention is preferably derived from castor oil, coconut oil, cottonseed oil, dehydrated castor oil, soybean oil, tall oil, rapeseed oil, sunflower oil, linseed oil, palm oil, tung oil, oiticica oil, safflower oil, olive oil, wood oil, corn oil, pumpkin oil, grapeseed oil, jojoba oil, sesame oil, walnut oil, hazelnut oil, almond oil, shea butter, macadamia oil, alfalfa oil, rye oil, peanut oil, copra oil, or argan oil.

The fatty acid or the mixture of fatty acids "derived from oil" is understood to mean a fatty acid present in the oil and/or fatty acids which can be obtained at the end of a chemical conversion. For example, heptanoic acid and/or 10-undecylenic acid can be obtained from castor oil, typically, by a step of thermal cracking of methyl ricinoleate which originates from the transesterification of castor oil.

Preferably, the $C_5$-$C_{12}$ saturated fatty acid according to the invention is selected from the group consisting of pentanoic acid, isovaleric acid, caproic acid, heptanoic acid, n-heptanoic acid, caprylic acid, pelargonic acid, capric acid, citric acid, tetrahydrofuran-2,5-dicarboxylic acid, tetrahydrofuran-3,5-dicarboxylic acid, azelaic acid, undecanedioic acid, and dodecanedioic acid.

Preferably, the $C_5$-$C_{12}$ saturated fatty acid according to the invention is n-heptanoic acid, more preferably Oleris® n-heptanoic acid (ARKEMA).

Preferably, the n-heptanoic acid is derived from castor oil.

Preferably, the $C_{10}$-$C_{12}$ unsaturated fatty acid according to the invention is selected from the group consisting of 10-undecylenic acid, and dodec-2-enedioic acid.

Preferably, the $C_{10}$-$C_{12}$ unsaturated fatty acid according to the invention is 10-undecylenic acid, more preferably Oleris® undecylenic acid (ARKEMA).

Preferably, the 10-undecylenic acid is derived from castor oil.

The weight ratio of the $C_5$-$C_{12}$ saturated fatty acid to the $C_{10}$-$C_{12}$ unsaturated fatty acid according to the invention is from 1:10 to 10:1, preferably 8:2 to 2:8, more preferably 7:3.

The polyol according to the invention can be chosen from any polyol well known to those skilled in the art. The polyol according to the invention may be of petrochemical origin or derived from renewable resources.

Preferably, the polyol according to the invention is an organic compound containing several hydroxyl groups.

According to one embodiment, the polyols do not refer to compounds which contain functional groups other than hydroxyl groups.

The polyol according to the invention is preferably selected from the group consisting of trimethylolpropane, trimethylolethane, pentaerythritol, dipentaerythritol, dipentaerythritol, tetrapentaerythritol and neopentyl glycol, or mixtures thereof.

The polyol derived from renewable resources according to the invention is preferably biodegradable. The polyol derived from renewable resources according to the invention may be a sugar polyol. Typically, the sugar polyol is a compound corresponding to the general chemical formula $C_nH_{2n+2}O_n$ and having at least two hydroxyl groups.

Preferably, the sugar polyol is selected from the group consisting of monosaccharides, disaccharides and trisaccharides.

Preferably, the monosaccharide according to the invention is selected from the group consisting of erythritol, xylose, arabinose, ribose, sorbitol, sorbitan, glucose, sorbose, fructose, xylitol and mannitol, more preferentially from the group consisting of xylose, arabinose, ribose, glucose, sorbose and fructose.

Preferably, the disaccharide according to the invention is selected from the group consisting of maltose, lactose, and sucrose.

The trisaccharide according to the invention is preferably selected from the group consisting of raffinose, maltotriose, and hydrogenated starch hydrolyzates.

More preferably, the sugar polyol according to the invention is erythritol.

The polyol according to the invention is preferably selected from the group consisting of erythritol, xylitol, mannitol, trimethylolpropane, trimethylolethane, pentaerythritol, dipentaerythritol, tripentaerythritol, tetrapentaerythritol, maltose, lactose, sucrose, raffinose, maltotriose and neopentyl glycol or mixtures thereof, more preferably from the group consisting of erythritol, xylitol, mannitol, trimethylolpropane, trimethylolethane, pentaerythritol, dipentaerythritol, tripentaerythritol, tetrapentaerythritol, and neopentyl glycol or mixtures thereof.

According to one embodiment, the sugar polyol according to the invention is obtained by hydrogenation of a sugar.

Preferably, the weight ratio of the polyol to the mixture of fatty acids is in the range of from 1:4 to 1:10. More preferably, the weight ratio of the polyol to the mixture of fatty acids is around 1:5.

Preferably, the ester according to the invention has an oxygen induction time measured in a differential scanning calorimeter at 150° C. of more than 2 hours.

Preferably, the ester according to the invention has an oxygen induction temperature measured in a differential scanning calorimeter of greater than 200° C.

Preferably, the ester according to the invention has a kinematic viscosity of from 14 to 30 mm$^2$/s at 40° C., and/or less than 6 mm$^2$/s at 100° C., which is measured according to the standard ISO 3104.

Preferably, the ester according to the invention has a pour point of less than −20° C.

Process

Preferably, the esterification process according to the invention comprises a step of esterifying at least one polyol according to the invention in the presence of a mixture of fatty acids in excess comprising at least one $C_5$-$C_{12}$ saturated fatty acid and at least one $C_{10}$-$C_{12}$ unsaturated fatty acid according to the invention, with or without a catalyst.

The esterification step according to the invention is preferably carried out at a temperature between 140° C. and 250° C. for a period of from 0.5 to 12 hours, preferably from 1 to 10 hours, more preferably from 2 to 8 hours.

The esterification step according to the invention is preferably carried out under an inert atmosphere.

The esterification step according to the invention is preferably carried out in a pressure range of from 30 mmHg to 760 mmHg.

The esterification process according to the invention may comprise a step of adding an absorbent such as alumina, silica gel, zeolites, activated carbon, and clay.

The process according to the invention may further comprise a step of adding water and base to simultaneously neutralize the residual organic and mineral acids and/or hydrolyze the catalyst. In this case, the process according to the invention may comprise a step of removing the water used by heating and placing under vacuum.

The process according to the invention may also comprise a step of filtering the solids of the ester mixture containing most of the excess acid mixture used in the esterification reaction.

The process according to the invention may comprise a step of removing the excess acids by steam extraction or by any other method of distillation and recycling of the polyol to the reaction vessel. Preferably, the compound obtained by the process according to the invention is purified by reduced-pressure distillation of the unreacted acid. The distillation is preferably carried out under vacuum for 15 to 60 minutes. The distillation is further preferably carried out at a temperature of between 140° C. and 180° C. The amount of free acid remaining after the distillation step can be reduced by treatment with epoxy esters, by neutralization with any suitable alkaline material such as lime, alkali metal hydroxides, alkali metal carbonates or basic alumina. When a treatment with epoxy esters is carried out, a second reduced-pressure distillation may be carried out to remove the excess epoxy ester. When an alkaline treatment is carried out, washing with water may be carried out to remove excess unreacted alkaline material.

The method according to the invention may comprise a step of removing any residual solid material from the ester extracted during a final filtration.

Preferably, the fatty acid mixture according to the invention is present in the reaction to form the ester according to the invention in an excess of around 10 to 50 mol %, preferably of around 10 to 30 mol %, relative to the amount of polyol used.

The process according to the invention can be carried out in the presence of a catalyst. The catalyst can be any catalyst well known to those skilled in the art for esterification reactions. Preferably, the catalyst is selected from the group consisting of tin chloride, sulfuric acid, p-toluenesulfonic acid, methanesulfonic acid, sulfosuccinic acid, hydrochloric acid, phosphoric acid, catalysts based on zinc, copper, tin, titanium, zirconium or tungsten; alkali metal salts such as sodium or potassium hydroxide, sodium or potassium carbonate, sodium or potassium ethoxide, sodium or potassium methoxide, zeolites and acidic ion exchangers, or mixtures thereof.

Use

The esters according to the invention are preferably used as they are as lubricant base or lubricant base oil.

The esters according to the invention may also be used as a mixture with other base oils, such as mineral oils, highly refined mineral oils, polyalphaolefins (PAO), polyalkylene glycols (PAG), phosphate esters, silicone oils, diesters, polyisobutylenes and polyol esters.

In particular, the esters according to the invention are useful for the preparation of a lubricant base composition. The lubricant base composition according to the invention can be used in all types of industries, in particular as automotive lubricants, as metalworking oils, as hydraulic oils, as turbine oils, or else as aircraft oils.

Preferably, the composition according to the invention may comprise a content of tetraesters greater than or equal to 80% by weight relative to the total amount of ester. More preferably, the composition may comprise a content of tetraesters greater than or equal to 93% by weight relative to the total amount of ester.

The composition according to the invention may comprise, in addition to the esters according to the invention, one or more additives. Preferably, the additives are selected from the group consisting of antioxidants, thermal stability improvers, corrosion inhibitors, metal deactivators, lubricant additives, viscosity index improvers, pour point depressants, detergents, dispersants, antifoaming agents, antiwear agents, and additives resistant to extreme pressure.

Preferably, the amount of additives in the composition according to the invention does not exceed 10% by weight, preferably 8% by weight, more preferably 5% by weight relative to the total weight of the lubricant base composition.

Preferably, the amount of antioxidants used is between 0.01% and 5% relative to the total weight of the lubricant base composition.

Preferably, the amount of corrosion inhibitors is between 0.01% and 5% by weight relative to the total weight of the lubricant base composition.

Preferably, the amount of metal deactivators is between 0.001% and 0.5% by weight relative to the total weight of the lubricant base composition.

Preferably, the amount of lubricant additives is between 0.5% and 5% by weight relative to the total weight of the lubricant base composition.

Preferably, the amount of viscosity index improvers is between 0.01% and 2% by weight relative to the total weight of the lubricant base composition.

Preferably, the amount of pour point depressants is between 0.01% and 2% by weight relative to the total weight of the lubricant base composition.

Preferably, the amount of detergents is between 0.1% and 5% by weight relative to the total weight of the lubricant base composition.

Preferably, the amount of dispersants is between 0.1% and 5% by weight relative to the total weight of the lubricant base composition.

Preferably, the amount of antifoaming agents is between 0.01% and 2% by weight relative to the total weight of the lubricant base composition.

Preferably, the amount of antiwear agents is between 0.01% and 2% by weight relative to the total weight of the lubricant base composition.

Preferably, the amount of additives resistant to extreme pressure is between 0.1% and 2% by weight relative to the total weight of the lubricant base composition.

Antioxidants and thermal stability improvers can be chosen from any antioxidants and thermal stability improvers well known to those skilled in the art. By way of example, the antioxidant and the thermal stability improver can be selected from the group consisting of:
- diphenylamine, dinaphthylamine, phenylnaphthylamine, in which the phenyl group or the naphthyl group can be substituted, for example by N,N'-diphenylphenylenediamine, p-octyldiphenylamine, p,p-dioctyldiphenylamine, N-phenylnaphthylamine, N-phenyl-2-naphthylamine, N-(p-dodecyl)phenyl-2-naphthylamine, di-1-naphthylamine, and di-2-naphthylamine groups;
- phenothiazines, such as N-alkylphenothiazines;
- imino(bisbenzyl); and
- hindered phenols such as 6-(t-butyl)phenol, 2,6-di(t-butyl)phenol, 4-methyl-2,6-di(t-butyl) phenol, 4,4'-methylenebis(2,6-di(t-butyl)phenol).

The metal deactivators can be chosen from any metal deactivators well known to those skilled in the art. By way of example, the metal deactivators can be selected from the group consisting of imidazole, benzamidazole, 2-mercaptobenzothiazole, 2,5-dimercaptothiadiazole, salicylidene-propylenediamine, pyrazole, benzotriazole, tolutriazole, 2-methylbenzamidazole, 3,5-dimethylpyrazole, and methylenebis(benzotriazole). Other examples of metal deactivators or corrosion inhibitors include:
- organic acids and esters, metal salts and anhydrides thereof, such as N-oleylsarcosine, sorbitan monooleate, lead naphthenate, dodecenylsuccinic acid and the partial esters and amides thereof, and 4-nonylphenoxyacetic acid;
- aliphatic and cycloaliphatic primary, secondary and tertiary amines and amine salts of organic and inorganic acids, such as oil-soluble alkylammonium carboxylates;
- heterocyclic compounds containing nitrogen, such as thiadiazoles, substituted imidazolines, and oxazolines;
- quinolines, quinones and anthraquinones;
- propyl gallate;
- barium dinonylnaphthalenesulfonate;
- derivatives of esters and amides of alkenylsuccinic anhydrides or acids, dithiocarbamates, dithiophosphates;
- amine salts of alkyl acid phosphates and derivatives thereof.

The lubricant additives can be chosen from any lubricant additives well known to those skilled in the art. Mention may be made, as examples of lubricant additives, of long-chain derivatives of fatty acids and of natural oils, such as esters, amines, amides, imidazolines and borates.

The viscosity index improvers can be chosen from any viscosity index improvers well known to those skilled in the art. Mention may be made, as examples of viscosity improvers, of polymethacrylates, copolymers of vinylpyrrolidone and of methacrylates, polybutenes and styrene-acrylate copolymers.

The pour point depressants can be chosen from any pour point depressants well known to those skilled in the art. Mention may be made, as examples of pour point depressants, of polymethacrylates such as methacrylate-ethylene-vinyl acetate terpolymers; alkylated naphthalene derivatives; and the products of urea-catalyzed Friedel-Crafts condensation with naphthalene or phenols.

The detergents and dispersants can be chosen from any detergents and dispersants well known to those skilled in the art. Mention may be made, as examples of detergents and dispersants, of polybutenylsuccinic acid amides; polybutenylphosphonic acid derivatives; aromatic sulfonic acids substituted by a long-chain alkyl and the salts thereof; and metal salts of alkyl sulfides, alkylphenols and condensation products of alkylphenols and aldehydes.

The anti-foaming agents can be selected from any anti-foaming agents well known to those skilled in the art. Mention may be made, as examples of anti-foaming agents, of polymers of silicone and certain acrylates.

The antiwear agents and additives resistant to extreme pressure can be chosen from any antiwear agents and additives resistant to extreme pressure. Mention may be made, as examples of antiwear agents and additives resistant to extreme pressure, of:
- sulfurized fatty acids and fatty acid esters, such as sulfurized octyl tallate;
- sulfurized terpenes;
- sulfurized olefins;
- organopolysulfides;
- organophosphorus derivatives comprising amine phosphates, alkyl acid phosphates, dialkyl phosphates, aminedithiophosphates, trialkyl and triaryl phosphorothionates, trialkyl and triaryl phosphines, and dialkyl phosphites such as amine salts of phosphoric acid monohexyl ester, amine salts of dinonylnaphthalenesulfonate, triphenyl phosphate, trinaphthyl phosphate, diphenyl cresyl phosphate and phenylphenyl phosphates, naphthyl diphenyl phosphate, triphenylphosphorothionate;
- dithiocarbamates, such as an antimony dialkyldithiocarbamate;
- chlorinated and/or fluorinated hydrocarbons and xanthates.

The invention will be further explained with the aid of the following nonlimiting examples.

EXAMPLES

The inventors have studied the properties of an ester according to the present invention for application in lubricants.

1. Preparation of the ester
   5 samples are tested:
   ester of erythritol and of a mixture of n-heptanoic acid and 10-undecylenic acid (ester according to the invention);
   ester of trimethylolpropane and of n-heptanoic acid (comparative example 1);

ester of trimethylolpropane and of 10-undecylenic acid (comparative example 2);

ester of trimethylolpropane and unsaturated fatty acids (comparative example 3-commercial product PRIOLUBE 2044® from CRODA);

ester of pentaerythritol and linear fatty acids (comparative example 4-commercial product NYCOBASE® 8410 from NYCO);

ester of pentaerythritol and branched fatty acids (comparative example 5-commercial product NYCOBASE® 1060X from NYCO).

Ester According to the Invention: Synthesis of a Tetraester of Erythritol and of a Mixture of Heptanoic and Undecylenic Acids with a Molar Excess of Acid Erythritol (16.4 g, 0.13 mol), n-heptanoic acid (64.3 g, 0.49 mol) and 10-undecylenic acid (27.8 g, 0.15 mol) with a 70/30 weight ratio are loaded into a 250 ml three-necked flask equipped with a stirrer, a thermometer, a condenser and a nitrogen inlet.

The reaction mixture was heated at 210° C. under a nitrogen atmosphere for a period of 5 h, until the theoretical amount of water was stable. Zirconium tetrabutanolate (1.35 g, at 80% in butanol, 1% by weight/total weight of the reactants) is then added batchwise to the reactor. The assembly is gradually placed under maximum vacuum at 190° C. for 2 hours 30 minutes to distil off the excess unreacted acid and results in 82.8 g of product.

A downstream treatment with activated basic alumina is carried out on the crude reaction product and results in an oil with an acid number of 0.02 mgKOH/g.

The kinematic viscosities, the viscosity index (VI) and the pour point of the product are evaluated and reported in table no. 2.

The chemical composition of the product was established by gas chromatography as follows: 93.6% tetraesters, 4.8% anhydroesters and 0.1% triesters.

Comparative Example 1: Synthesis of an Ester of Trimethylolpropane and of n-Heptanoic Acid with a Molar Excess of Acid Trimethylolpropane (53.8 g, 0.4 mol) and n-heptanoic acid (181.5 g, 1.38 mol) are loaded into a 500 ml three-necked flask equipped with a stirrer, a thermometer, a condenser and a nitrogen inlet. The reaction mixture was heated at 185° C. under a nitrogen atmosphere for a period of 3 h, until the theoretical amount of water was collected.

Zirconium tetrabutanolate (1.5 g, at 80% in butanol, 0.5% by weight/total weight of the reactants) is then added batchwise to the reactor. The assembly is gradually placed under maximum vacuum at 185° C. for 3 hours 30 minutes to distil off the excess unreacted acid and results in 187.4 g of product. A downstream treatment with activated basic alumina is carried out on the crude reaction product and results in an oil with an acid number of 0.1 mgKOH/g. The chemical composition of the product was established by gas chromatography as follows: 98.8% trimethylolpropane triheptanoate and 0.03% trimethylolpropane diheptanoate.

Comparative Example 2: Synthesis of a Trimethylolpropane Ester of 10-Undecylenic Acid with a Molar Excess of Acid Trimethylolpropane (40.4 g, 0.30 mol) and 10-undecylenic acid (218 g, 1.17 mol) are loaded into a 500 ml three-necked flask equipped with a stirrer, a thermometer, a condenser and a nitrogen inlet. The reaction mixture was heated at 185° C. under a nitrogen atmosphere for a period of 3 h, until the theoretical amount of water was collected. Zirconium tetrabutanolate (3.2 g, at 80% in butanol, 1% by weight/total weight of the reactants) is then added batchwise to the reactor. The assembly is gradually placed under maximum vacuum at 185° C. for 3 hours 30 minutes to distil off the excess unreacted acid and results in 195.3 g of product.

A downstream treatment with activated basic alumina is carried out on the crude reaction product and results in an oil with an acid number of 1.8 mgKOH/g. The chemical composition of the product was established by gas chromatography as follows: 98.3% trimethylolpropane triundecylenate and 0.99% trimethylolpropane diundecylenate.

2. Measurement of the Oxidation Resistance

Oxidation stability is determined via two measurements: oxygen induction time and oxygen induction temperature. Oxygen induction time and oxygen induction temperature are measured in a differential scanning calorimeter (DSC).

For the measurement of the oxygen induction time, the sample is heated to 150° C. and then maintained at constant temperature. It is then exposed to an oxidizing atmosphere. The time between contact with oxygen and the onset of oxidation is the oxygen induction time.

For the measurement of the oxygen induction temperature, the sample is heated with a constant heating rate under an oxidizing atmosphere until the reaction begins. The oxygen induction temperature is the temperature at which the oxidation reaction begins.

The results are presented in Table 1 below:

TABLE 1

| | measurement of the oxidation resistance | | |
|---|---|---|---|
| Product | Ester of erythritol and of a mixture of n-heptanoic acid and 10-undecylenic acid | Comparative example 1: ester of trimethylolpropane and of n-heptanoic acid | Comparative example 2: ester of trimethylolpropane and of 10-undecylenic acid |
| Oxygen induction time at 150° C. | >2 hours | >2 hours | >2 hours |
| Oxygen induction temperature (° C.) | 203 | 196 | 182 |

The measurements show that the oxygen induction times at 150° C. of the three samples are similar. The ester according to the invention has a higher oxygen induction temperature than comparative examples 1 and 2. Consequently, the ester according to the invention has better oxidation resistance properties than the usual esters synthesized from a non-biobased alcohol.

3. Measurement of the Kinematic Viscosity

The kinematic viscosity was measured at 40° C. and at 100° C. according to the standard ISO 3104.

The results, expressed in mm²/s, are presented in table 2 below.

4. Measurement of the Viscosity Index

The viscosity index (unitless) is measured according to the test method described in standard ASTM D 2270. The results are presented in table 2 below.

5. Measurement of the Pour Point

The pour point, expressed in ° C., is measured according to the standard ISO 3016. The results are presented in table 2 below.

TABLE 2 measurement of the kinematic viscosity, viscosity index and pour point.

| Designation | Ester of erythritol and of a mixture of n-heptanoic acid and 10-undecylenic acid | Comparative example 3: ester of trimethylolpropane and of unsaturated fatty acids | Comparative example 4: ester of pentaerythritol and of linear fatty acids | Comparative example 5: ester of pentaerythritol and of branched fatty acids |
|---|---|---|---|---|
| Kinematic viscosity at 40° C. (mm²/s) ISO 3104 | 23.9 | 85 | 29.1 | 250 |
| Kinematic viscosity at 100° C. (mm²/s) ISO 3104 | 5.2 | 12.4 | 5.8 | 20 |
| Viscosity index (VI) ASTM D2270 | 154 | 142 | 147 | 92 |
| Pour point (° C.) ISO 3016 | −27 | −3 | −6 | −25 |

These examples show that the ester according to the invention synthesized from substances of renewable origin has the lowest kinematic viscosities at 40° C. and 100° C. and also the highest viscosity index, which means that the lubricant base according to the invention has a temperature-stable viscosity.

The lubricant base of the invention displays the lowest pour point, compared to those of the comparative examples synthesized from alcohols derived from the petroleum industry and linear or else branched, unsaturated fatty acids.

The invention claimed is:

1. An ester of at least one polyol and of a mixture of fatty acids comprising at least one $C_5$-$C_{12}$ saturated fatty acid and 10-undecylenic acid, wherein the weight ratio of the $C_5$-$C_{12}$ saturated fatty acid to the 10-undecylenic acid is 1:10 to 10:1.

2. The ester as claimed in claim 1, wherein the mixture comprises at least 50% by weight of linear fatty acids.

3. The ester as claimed in claim 1, wherein the $C_5$-$C_{12}$ saturated fatty acid is n-heptanoic acid.

4. The ester as claimed in claim 1, wherein the weight ratio of the $C_5$-$C_{12}$ saturated fatty acid to the 10-undecylenic acid is 8:2 to 2:8.

5. The ester as claimed in claim 1, wherein the weight ratio of the $C_5$-$C_{12}$ saturated fatty acid to the 10-undecylenic acid is 7:3.

6. The ester as claimed in claim 1, wherein the weight ratio of the polyol to the mixture of fatty acids is at least 1:5.

7. The ester as claimed in claim 1, wherein the $C_5$-$C_{12}$ saturated fatty acid and the 10-undecylenic acid are derived from renewable resources.

8. The ester as claimed in claim 3, wherein the $C_5$-$C_{12}$ saturated fatty acid and the 10-undecylenic acid are derived from castor oil.

9. The ester as claimed in claim 1, wherein the polyol is selected from the group consisting of sorbitol, erythritol, xylitol, mannitol, trimethylolpropane, trimethylolethane, pentaerythritol, dipentaerythritol, tripentaerythritol, tetrapentaerythritol, maltose, lactose, sucrose, raffinose, maltotriose, and neopentyl glycol or mixtures thereof.

10. The ester as claimed in claim 1, wherein the polyol is derived from a renewable resource.

11. The use of the ester of at least one polyol and of a mixture of fatty acids comprising at least one $C_5$-$C_{12}$ saturated fatty acid and 10-undecylenic acid as defined in claim 1 as a lubricant base.

12. A composition of a lubricant base comprising an ester of at least one polyol and of a mixture of fatty acids comprising at least one $C_5$-$C_{12}$ saturated fatty acid and 10-undecylenic acid as defined in claim 1.

13. A process for preparing an ester comprising the esterification of a mixture of fatty acids comprising at least one $C_5$-$C_{12}$ saturated fatty acid and 10-undecylenic acid with at least one polyol, optionally in the presence of a catalyst, wherein the weight ratio of the $C_5$-$C_{12}$ saturated fatty acid to the 10-undecylenic acid is 1:10 to 10:1.

14. An ester of at least one polyol and of a mixture of fatty acids comprising at least one $C_5$-$C_{12}$ saturated fatty acid and 10-undecylenic acid obtained by the process as claimed in claim 13.

15. The ester as claimed in claim 1, wherein the at least one polyol is erythritol.

16. The ester as claimed in claim 1, wherein the at least one $C_5$-$C_{12}$ saturated fatty acid is heptanoic acid.

17. The ester as claimed in claim 1, wherein the at least one polyol is erythritol and the at least one $C_5$-$C_{12}$ saturated fatty acid is heptanoic acid.

18. The ester as claimed in claim 1, further comprising an additive selected from the group consisting of a thermal stability improver, a lubricant additive, a viscosity index improver, a pour point depressant, and a detergent.

* * * * *